United States Patent [19]
Igarashi et al.

[11] Patent Number: 5,677,189
[45] Date of Patent: Oct. 14, 1997

[54] METHOD FOR QUANTIFYING SPHINGOSINE AND FOR DIAGNOSING PLATELET ACTIVATION

[75] Inventors: Yasuyuki Igarashi; Yutaka Yatomi; Hideki Ohta, all of Seattle; Sen-Itiroh Hakomori, Mercer Island, all of Wash.

[73] Assignee: Oncomembrane, Inc., Seattle, Wash.

[21] Appl. No.: 496,471

[22] Filed: Jun. 29, 1995

[51] Int. Cl.$^6$ .................................................. G01N 33/50
[52] U.S. Cl. ............................. 436/57; 436/63; 436/71; 436/111
[58] Field of Search ..................... 436/57, 63, 71, 436/111, 112, 178

[56] References Cited

PUBLICATIONS

Yatomi, Y. et al. Analytical Biochemistry, vol. 230, pp. 315–320 (1995) 1995.
Yatomi, Y. et al. Blood, vol. 86, No. 1, pp. 193–202 (Jul. 01, 1995) Jul. 1995.
Stryer, L. "Biochemistry" W.H. Freeman and Company, New York, pp. 461–462 (1981) 1981.
Yatomi, Y. et al. "Quantitative Measurement of Sphingosine 1–Phosphate in Biological Samples by Acylation with Radioactive Acetic Anhydride" Analytical Biochemistry, vol. 230, pp. 315–320 (1995) 1995.
Amemiya, Y. et al. "Imaging Plate Illumnates Many Fields" Nature, vol. 336, pp. 89–90 (1988) Nov. 03, 1988.
Merrill, A.H. Jr. et al. "Quantitation of Free Sphingosine in Liver by High–Performance Liquid Chromatography" Analytical Biochemistry, vol. 171, pp. 373–381 (1988) 1988.
Vunnam, R.R. et al. "Short Chain Ceramides as Substrates for Glucocerebroside Synthetase" Biochimica et Biophysica Acta, vol. 573, pp. 73–82 (1979) 1979.
Yutaka Yatomi et al., "N,N–Dimethylsphingosine Inhibition of Sphingosine Kinase and Sphingosine 1–Phosphate Activity in Human Platelets", Biochem., 35:626–633, (1996).
Hideki Ohta et al., "Quantification of Free Sphingosine in Culture Cells by Acylation with Radioactive Acetic Anhydride", Analyt. Biochem., 222:489–494, (1994).
Yasayuki Igarashi et al., "The Relationships of Sphingosine–1–Phosphate Content in the Plasma from Platelet Samples with Transfusion Reactions", (Abstract of paper presented at the Second Meeting of European Haematology Association, Paris, France, 29 May—1 Jun. 1996).

*Primary Examiner*—Jeffrey Snay
*Attorney, Agent, or Firm*—Sughrue, Mion, Zinn, Macpeak, and Seas

[57] ABSTRACT

A method of detecting sphingosines and platelet activation is disclosed.

16 Claims, No Drawings

METHOD FOR QUANTIFYING SPHINGOSINE AND FOR DIAGNOSING PLATELET ACTIVATION

Portions of the research described herein were supported in part by a grant from the National Cancer Institute, National Institutes of Health, Department of Health and Human Services.

FIELD OF THE INVENTION

The instant invention relates to an assay for quantifying for example, sphingosine and sphingosine-1-phosphate which can be used to ascertain platelet activation.

BACKGROUND OF THE INVENTION

Sphingosine (Sph or S) and physiologically active derivatives thereof, such as sphingosine-1-phosphate (Sph-1-P or S-1-P) have proven difficult to measure in biologic samples, such as cells and serum, in part due to the many forms and functions of the molecules and the fluctuating amounts thereof.

Current methods for detecting and measuring Sph require tedious protocols and costly equipment, such as HPLC, following derivatization of the sphingosine (Kobayashi et al., Eur. J. Biochem. 172: 747, 1988; Merrill, Jr. et al., Anal. Biochem. 171: 373, 1988; Van Veldhoven et al., FEBS Lett. 350: 91, 1994; Lagana et al., Chromatog. 39: 85, 1994) or reliance on enzymatic reaction (Van Veldhoven et al., Anal. Biochem. 183: 177, 1989; Spiegel, J. Lipid Mediat. 8: 169, 1993; Olivera et al., Anal. Biochem. 223: 306, 1994). There is no known method to detect and to measure Sph-1-P.

Sph-1-P is the initial product of catabolism of Sph by Sph kinase (Buehrer & Bell, J. Biol. Chem. 267: 3154, 1992; Adv. Lipid Res. 26: 59, 1993; Stoffel et al., Hoppe. Z. Physiol. Chem. 351: 635, 1970) which then is cleaved by Sph-1-P lyase to a fatty aldehyde and ethanolamine phosphate (Van Veldhoven & Mannaerts, J. Biol. Chem. 266: 12502, 1991; Van Veldhoven & Mannaerts, Advances Lipid Res. 26: 69, 1993; Van Veldhoven & Mannaerts, Biochem J. 299: 597, 1994) or dephosphorylated by a sphingosine phosphatase (Van Veldhoven & Mannaerts, Biochem J. 299: 597, 1994).

The phosphorylated sphingoid base, Sph-1-P, is not only an intermediary catabolite but also an important bioactive compound. Sph-1-P stimulates DNA synthesis and cell division in quiescent cultures of Swiss 3T3 fibroblasts, possibly via induction of $Ca^{2+}$ mobilization or enhanced phosphatidic acid synthesis (Zhang et al., J. Cell Biol. 114: 155, 1991; Desai et al., J. Biol. Chem. 267: 23122, 1992).

Sph-1-P also has been implicated as a novel second messenger in PDGF-dependent and serum-dependent fibroblast cell growth (Olivera & Spiegel, Nature 365: 557, 1993). In BALB/c 3T3 cells, Sph kinase was reported to be activated by phorbol esters independent of protein kinase C (Mazurek et al., Biochem. Biophys. Res. Commun. 198: 1, 1994). Another important bioactivity of Sph-1-P is reported to be inhibition of conditioned medium-induced motility and phagokinesis of certain tumor cells by unknown mechanisms (Sadahira et al., Proc. Natl. Acad. Sci. U.S.A. 89: 9686, 1992; Sadahira et al., FEBS Lett. 340: 99, 1994).

Platelets are cell fragments containing most of the usual organelles but lacking a nucleus. Platelets are very sensitive to many diverse agonists and react within seconds of exposure to those stimuli. The process of platelet activation in the circulation is highly regulated. Platelets play a central role in hemostasis. Overactive platelets are implicated in the pathogenesis of harmful processes such as atherosclerosis and thrombosis (Siess, Physiol. Rev. 69: 58, 1989; Van Zanten et al., J. Clin. Invest. 93: 615, 1994).

Platelets, which lack the ability to proliferate, possess a very active sphingosine kinase (Buehrer & Bell, J. Biol. Chem. 267: 3154, 1992; Stoffel et al., Hoppe-Seyler's Z. Physiol. Chem. 354: 562, 1973; Stoffel et al., Hoppe-Seyler's Z. Physiol. Chem. 354: 1311, 1973) and practically no lyase activity for degradation of Sph-1-P to a fatty aldehyde and ethanolamine phosphate (Stoffel et al., Hoppe-Seyler's Z. Physiol. Chem. 351: 635, 1970; Stoffel et al., Hoppe-Seyler's Z. Physiol. Chem. 354: 1311, 1973). Those observations suggest an important role(s) of Sph-1-P in functional responses of highly differentiated cells, such as platelets.

It now has been determined that Sph-1-P induces platelet activation. Furthermore, when platelets are incubated with radiolabeled Sph, Sph-1-P is formed rapidly and released into the extracellular environment on stimulation with physiological agonists, suggesting that the phosphorylated sphingosine may act as a local mediator in control of hemostasis and thrombosis. That observation enables use of a new assay for Sph-1-P to determine the extent of platelet activation in a sample.

SUMMARY OF THE INVENTION

It is an object of the instant invention to provide an assay for sphingosine.

It is another object of the instant invention to provide an assay for sphingosine-1-phosphate.

Another object of the instant invention is to provide an assay of platelet activation.

A further object of the instant invention is to provide a method for activating platelets.

Those and other objects have been achieved in the development of an assay for sphingosines, such as sphingosine-1-phosphate, relying on N acylation of sphingosine, wherein the acyl group is labelled and serves as the reporter molecule. Because S-1-P may induce platelet activation and is released by activated platelets, the sphingosine assay can be used to detect and to quantify the degree of platelet activation in a sample.

DETAILED DESCRIPTION OF THE INVENTION

The term, "sphingosine", is used to denote sphingosine and biologically active sphingosine derivatives.

The term, "sphingosine derivatives", is meant to encompass physiologically compatible molecules comprising the sphingosine features of a hydrophobic, linear hydrocarbon chain of about fifteen carbon atoms and a 2-amine group. Examples include sphingosine-1-phosphate and dihydroxysphingosine.

Described herein is a simple and sensitive method for quantifying the mass of sphingosine, and for example, sphingosine-1-phosphate, present in cellular lipid extracts. Sphingosine has a free amino group which is acylated with labelled acyl anhydride, such as acetic anhydride. The method is based on selective and quantitative conversion of sphingosine to a ceramide, such as $C_2$-ceramide using the example hereinabove. Alkaline treatment of the sample after the acylation step is preferred to reduce background by removing the remaining unreacted acyl anhydride and hydrolyzing any ester linkages formed during acylation. The assay allows quantifying sphingosine over a range of 10 to 1500 pmol.

The instant assay operates preferably with sphingosine substrates with a free amino group. Sphingosine derivatives lacking a free amino group nevertheless can be assayed by incorporating a pretreatment step to remove substituents preexisting as the amine function, such a pretreatment step might be, for example, wherein the lipid extract is treated, for example, with strong base, prior to reacting with labelled acyl anhydride.

Biological samples contain other amino-containing lipids (e.g., phosphatidylathanolamine, phosphatidylserine and plasmalogen which might interfere with the acylation of sphingosine. Those lipids (except plasmalogen) are removed during the base treatment procedures.

Plasmalogen is converted to lysoplasmalogen by base treatment which is acylated with acetic anhydride. But the interference from plasmalogen with the determination of sphingosines is negligible. About 500 nmol of phosphatidylethanolamine containing approximately 60% plasmalogen is estimated to be far more than the plasmalogen content of $10^6$–$10^7$ of any kind of cells (L. A. Horrocks, in Ether Lipids, Snyder, ed., pp. 177–272, Academic Press, NY, 1972) because when added to samples containing varying amounts of sphingosine, no interference with the sphingosine standard curve will be observed.

Also, sphinganine in cells is considered to be present in much smaller amounts than is sphingosine (K. A. Karlsson, Chem. Phys. Lipids 5: 6, 1970; A. H. Merrill, Jr. et al., J. Biol. Chem. 268: 27299, 1993).

Samples can be obtained from a variety of sources, such as, cultured cells, a blood sample, cell suspension obtained by triturating a solid tissue piece and the like. A desired amount of cells, for example, 1–10×$10^6$ cells, is harvested and lipids are extracted using known techniques, for example, see Merrill et al., supra. The same procedures can be applied to substantially cell-free preparations, such as serum, plasma and spent tissue culture medium.

Thus, the cells are washed with medium or salt solution and then exposed to an organic solvent to effect lipid extraction, preferably a volatile organic solvent. A suitable solvent is chloroform or a mixture of chloroform and methanol at a ratio of 1:2. The suspension can be treated mechanically to enhance cell lysis, such as by sonication.

The dissolved lipids are treated with mild base to reduce background. A suitable base is sodium hydroxide at a concentration of 0.1N through 1N, and preferably at about 0.2N, or ammonium hydroxide. The incubation can occur at room temperature for about one hour. The alkali is dissolved in a solvent miscible with the organic solvent used for extracting lipids, but removable when partitioned with an aqueous solvent to enable removal of contaminants and excess alkali.

Thus alkali can be dissolved in, for example, an alcohol, such as, methanol or ethanol, which can be removed following incubation by adding to the extract, an aqueous solvent, such as water or a salt solution, such as a 1M sodium chloride solution.

The desired sphingosine species will partition predictably based on the physical properties thereof and of the solvents. For example, sphingosine-1-phosphate can be found in an aqueous phase and sphingosine can be found in an organic phase providing clear discrimination of closely related species. If the aqueous phase is acidified, for example, by adding concentrated HCl, the aqueous soluble species can be shifted to the organic phase. That can facilitate concentration and solvent removal of samples containing charged species.

Then, the samples can be dried by, for example, evaporation under a $N_2$ stream, if a volatile organic solvent is used.

The dried samples then are resuspended in a solution of dilute base (0.002N-0.014N NaOH, for example) and labelled acyl anhydride. The acyl anhydride can be labelled using any of a variety of art-recognized means. For example, acetic anhydride or propionic anhydride can carry a $^3$H or $^{14}$C atom. Radiolabeled acetic anhydride is available commercially, such as from New England Nuclear, Boston, Mass. Preferably the radiolabeled acetic anhydride is stored in benzene at −80° C. and diluted to the appropriate concentration with an organic solvent, such as distilled chloroform stored above 4 Å molecular sieves just prior to use.

Acylation is allowed to proceed for a suitable period of time, for example, 1–3 hours, at an appropriate temperature, for example, room temperature to about 40° C.

Following the incubation, excess anhydride is hydrolyzed by exposure of the reaction mix for about an hour to strong base, for example, 0.18–0.5N NaOH in methanol.

If desired, the labelled ceramide can be removed by partitioning with organic and aqueous solvents. The organic fraction containing the ceramide is separated, the organic solvent removed and the remainder suspended in a small volume of solvent. A suitable solvent is a 4:1 solution of chloroform:methanol.

Samples can be spotted on a thin layer chromatography (TLC) plate, commercially available, for separation and identification practicing known techniques. Separation is allowed to occur using an appropriate solvent.

If the acyl anhydride is labelled radioactively, the compounds can be detected by autoradiography using X-ray film with enhancing agents, such as Resolution TLC spray (L. M. Corp., Chestnut Hill, Mass.) and intensifying screens. The amount of radioactivity can be quantified by scraping labelled spots into a suitable scintillation fluid and measured in a liquid scintillation counter.

Recently, an imaging plate system using phosphorimaging technology was developed (Amemiya & Miyahara, Nature 336: 89, 1988). The system is useful for quantifying of $^{32}$P-labelled or $^{14}$C-labelled samples with high sensitivity and accuracy (Maskos & Southern, Nucleic Acids Res. 21: 4663, 1993). The procedure of scraping from TLC plates and counting with a liquid scintillation counter can be replaced with imaging data using digital values from the imaging plate, easily processed by computer. When [$^{14}$C]acyl anhydride is used for acylation instead of [$^3$H]acyl anhydride, use of the imaging plate may facilitate the instant method for quantifying sphingosine.

An alternative means for detecting the separated species is by HPLC, using for example a refractive index detector.

Other suitable detecting means can be used depending on the nature of the label attached to the acyl anhydride, such as fluorescent tags, enzymes, visual markers, such as viruses, and the like. Alternatively, stains can be used to distinguish species wherein the discriminating patterns of the known authentic species serve as a reference. Thus, a fluorescent compound specific for sphingosine can be used in conjunction with an ultraviolet light source.

The amount of sphingosine in a sample can be derived by reference to a standard curve comparing the level of labelling, for example, measuring radioactivity, relative to sphingosine concentration.

For example, the instant assay is quantitative and provides a linear relationship of sphingosine acylation from at least 30 pmol to 10 nmol for sphingosine-1-phosphate. The assay can quantify Sph-1-P from biologic samples over a range of at least 100 pmol to 10 nmol (the highest level tested).

Sph-1-P has a distinct effect on platelet activation. When human platelets are exposed to 40 µM Sph-1-P, the platelets aggregate. Aggregation is abolished if extracellular fibrinogen is omitted from the reaction or 1 mM EGTA is incorporated rather than 1 mM $Ca^{+2}$ in the reaction.

Sph-1-P also induces a change in platelet shape from discoid to spheroid bodies with numerous pseudopodia, comparable to that observed on exposing platelets to collagen, a known platelet agonist (Siess, Physiol Rev. 69: 58, 1989). Sphingosine, ceramide (type III), $C_2$-ceramide, $C_8$-ceramide, dimethylsphingosine and sphingomyelin do not elicit platelet aggregation or shape change.

Weak platelet agonists often interact in synergistic fashion to provide an efficient amplification mechanism for platelet activation (Siess, supra; Siess, News Physiol. Sci. 6: 51, 1991). That is particularly true when platelets are challenged with epinephrine or ADP, which are classified as weak platelet agonists. (Siess, 1991, supra; Lanza et al., Am. J. Physiol. 255: H1276, 1988; Shourani & Hall, Trends Pharm. Sci. 15: 103, 1994) Generally, ADP alone induces full aggregation at concentrations above 5 µM. At lower concentrations, such as 1 µM, ADP produces little aggregation. At 20 µM, Sph-1-P induces low levels of aggregation. In the presence of subthreshold concentrations of both of those agents together, marked aggregation occurs. A similar synergistic effect is seen when the stimuli used are Sph-1-P (20 µM) and epinephrine (2 µM).

Thus, Sph-1-P can be used to activate platelets. A suitable amount of Sph-1-P, in a biologically compatible liquid medium, such as tissue culture medium, physiologic saline or water, is applied to platelets to enable activation thereof, as with any other agonist. The application step can occur in a host by administering Sph-1-P using known means and methods, for example, intravenous or intramuscular injection. Formulation of Sph-1-P into a suitable composition and methods for applying same are non-critical aspects of the invention known in the art and are practiced without undue experimentation.

Also, exposure of platelets to agonists results in release of Sph-1-P from platelets. Platelets lack sphingosine-1-phosphate lyase which degrades Sph-1-P. Hence, intraplatelet Sph-1-P levels tend to remain relatively static in resting platelets. Moreover, the basal mass of Sph-1-P in platelets is on the order of 1.4 nmol/$10^9$ platelets and four times higher than the level of sphingosine and the Sph-1-P/phospholipid ratio is on the order of ten times greater than the ratio found in neutrophils or erythrocytes. Hence, Sph-1-P release by platelets is an excellent marker for platelet activation.

Plasma and serum also were found to contain S-1-P. In one set of experiments, plasma was found to contain 0.197 nmol/ml of Sph-1-P whereas serum contained 0.405 nmol/ml of Sp-1-P, consistent with the expectation following clotting.

Platelets activated with thrombin or collagen release a substantial part of newly-formed Sph-1-P into the medium, whereas ceramide and Sph remain associated with the cells. In platelets stimulated with 0.5 U/ml of thrombin for 5 min, 5.4±1.4% (mean±SD, n=5) of Sph-1-P formed is released into the medium. Sph-1-p release from thrombin-activated platelets is inhibited by preincubation with staurosporine, a potent protein kinase inhibitor (Yatomi et al. Biochim. Biophys. Acta 1212: 337, 1994; Yatomi et al. Biochem. J. 285: 745, 1992; Watson et al. Biochem. J. 249: 345, 1988).

The invention now will be described by way of the following non-limiting examples. Unless otherwise indicated, amounts are on a w/w, w/v or v/v basis according to the known state of the compounds.

EXAMPLES

Example 1

Sphingosine was extracted from cultured cells by a known method (Merrill et al. Anal. Biochem. 171: 373, 1988). Cells ($1\times10^6$ to $1\times10^7$) were harvested, washed with phosphate-buffered saline (PBS), resuspended in 0.1 ml of PBS and transferred to 20×125 mm screw-cap (standard borosilicate tubes with Teflon caps) test tubes. Three milliliters of chloroform/methanol (1/2, v/v) then were added, the contents mixed thoroughly and sonicated for 5 min. Phases were separated by adding 2 ml each of chloroform and 1M NaCl. The upper phase was discarded and 3 ml of 0.2N NaOH in methanol were added to the lower chloroform phase. After incubation at room temperature for 1 h, phases were separated by adding 3 ml each of chloroform and 1M NaCl. The lower chloroform phase was washed three times with chloroform/methanol/water (3/48/47) and transferred to 13×100 mm screw cap (standard borosilicate tubes with Teflon caps) test tubes. Samples from the chloroform phase were evaporated under $N_2$.

Example 2

Dried samples were dissolved in 40 µl of 0.008N NaOH in redistilled methanol/10 mM solution of [$^3$H]acetic anhydride (1/1) by sonication. Acetic anhydride was stored in benzene at −80° C. and diluted with distilled chloroform stored over 4 Å molecular sieves prior to use. Acylation proceeded for 1 h at 37° C. The remaining anhydride was hydrolyzed by addition of 0.2 ml of 0.2N NaOH in methanol. Following a 1 h incubation at room temperature, $C_2$-ceramide was extracted by addition of 0.78 ml of methanol, 0.98 ml of chloroform and 0.9 ml of 1M NaCl. The lower chloroform phase was washed twice with 1 ml of chloroform/methanol/water (3/48/47). Samples from the chloroform phase were evaporated under $N_2$ and dissolved in 40 µl of chloroform/methanol (4/1).

Samples were spotted on TLC plates. Plates were developed with chloroform/methanol/7N $NH_4OH$/water (80/20/0.5/0.5) and air-dried. After spraying with Resolution TLC, plates were exposed to Kodak X-Omat film at −80° C. TLC plates were sprayed with water, radioactive spots corresponding to [$^3$H]$C_2$-ceramide were scraped and counted in 4 ml of Aquasol liquid scintillation fluid. Sphingosine levels in cell extracts were calculated by extrapolation from sphingosine standards which were run through the same procedures (i.e. extraction, base treatment and acylation).

Example 3

To assess the concentration of acetic anhydride sufficient for acylation of sphingosine, 500 pmol of [$^3$H]sphingosine were dissolved in a mixture of 20 µl of 0.008N NaOH in methanol and 20 µl of various amounts of acetic anhydride in benzene/chloroform (1/9). After incubation for 1 h at 37° C., samples were chromatographed on TLC plates using chloroform/methanol/7N $NH_4OH$/water (80/20/0.5/0.5) as developing solvent and subjected to radioautography. To ensure the purity and identity as $C_2$-ceramide of the acylated product from cell extracts, $1\times10^7$ cells were subjected to the entire procedure. Radioactive spots corresponding to [$^3$H]$C_2$-ceramide were scraped from TLC plates, reextracted with chloroform, chromatographed on TLC plates using chloroform/methanol (9/1) or chloroform/methanol/acetic acid/water (100/80/20/5) as a developing solvent and subjected to autoradiography after spraying with Resolution TLC.

Optimal conditions for acylation of sphingosine were determined using [$^3$H]sphingosine to monitor the reaction. Acylation was complete in 1 h at 37° C. when 100 nmol or more acetic anhydride was used. When 10 μmol or more acetic anhydride was used, some acylation of free hydroxyl occurred. Therefore, 200 nmol of [$^3$H]acetic anhydride were used routinely thereafter for the assay of sphingosine.

Acylation was performed under weak alkaline conditions. The presence of 0.004N NaOH in the reaction mixture improved acylation of sphingosine. Also 2.5% triethylamine was tested as a base but was less efficient than NaOH.

Known quantities of sphingosine (from 10 to 400 pmol) were carried through the acylation procedure with 200 nmol of [$^3$H]acetic anhydride. Following treatment of samples with NaOH, which destroys excess anhydride and hydrolyzes ester linkages formed during the acylation, [$^3$H]C$_2$-ceramide was extracted quantitatively into the chloroform phase. Although tritiated acetic anhydride has been found to develop nonvolatile residues with time, [$^3$H]C$_2$-ceramide was separated well from the unknown radioactive residues by TLC using chloroform/methanol/7N NH$_4$OH/water (80/20/0.5/0.5) as a developing solvent. The amount of [$^3$H]C$_2$-ceramide formed was proportional to added sphingosine. When sphingosine was carried through the whole procedure (i.e. extraction, base treatment and acylation) recovery was 50–60%. The assay allowed quantification of sphingosine over a range from 10 to 1500 pmol.

Example 4

Possible interference from various lipid components (i.e. phosphatidylethanolamine, phosphatidylserine, plasmalogen and sphingosine-1-phosphate) was tested by adding 500 nmol of each of those lipids to the amounts of sphingosine used to generate the standard curve. (The molecular content of phosphatidylethanolamine which contained plasmalogen was estimated roughly by using the molecular weight of phosphatidylethanolamine (dioleoyl) as a representative of molecular weight.) To test whether alkaline conditions cause degradation of complex sphingolipids to sphingosine, 100 μg quantities of sphingomyelin, ganglioside or ceramide were treated similarly with base and acylated with [$^3$H] acetic anhydride as described above.

Alkaline hydrolysis of cellular lipid extracts was performed to cleave acylglycerolipids. Phosphatidylethanolamine and phosphatidylserine were removed by alkaline hydrolysis and washing. Although sphingosine-1-phosphate was not cleaved by alkaline hydrolysis, sphingosine-1-phosphate was extracted into the aqueous phase during the extraction procedures and removed from the chloroform phase after several washings. When 500 nmol each of phosphatidylserine and sphingosine-1-phosphate were carried through the entire procedure, no acylated products were detected. On the other hand, plasmalogen was converted to lysoplasmalogen by treatment with base and acylated with acetic anhydride. However, the standard curve of sphingosine was not affected by adding 500 nmol of phosphatidylethanolamine which contained approximately 60% plasmalogen to the samples. An acylated product corresponding to N-acetylated lysoplasmalogen and C$_2$-ceramide was observed in lipid extracts from cells in two different developing solvents: (a) chloroform/methanol/7N NH$_4$OH/water (85/15/0.5/0.5) and (b) chloroform/methanol/acetic acid/water (100/60/20/5). C$_2$-ceramide and N-acetylated lysoplasmalogen were resolved by TLC.

Example 5

Cells ($10^6$) were pelleted by centrifugation and resuspended in 0.8 ml of 0.9% (w/v) NaCl. Then, 3 ml of chloroform/methanol (1/2) were added and mixed thoroughly. Phases were separated by adding 1 ml each of chloroform and 1M NaCl. The lower chloroform phase was washed two times with 2 ml of 1M NaCl and the phospholipid content thereof was estimated by the method of Ames and Dubin (Ames & Dubin, J. Biol. Chem. 235: 769, 1960).

Example 6

Sph-1-P was prepared from sphingosylphosphocholine with bacterial phospholipase D as described previously (Van Veldhoven et al. J. Lipid Res. 30: 611, 1989). N-acetyl-Sph (C$_2$-ceramide),N-octanoyl ceramide(C$_8$-ceramide)(Vunnam et al. Biochim. Biophys. Acta 573: 73, 1979) and DMS (Igarashi et al. Biochemistry 28: 6796, 1989) were synthesized as described. [$^{14}$C]DMS was prepared from Sph with $^{14}$CH$_3$I and K$_2$CO$_3$ reacted in methanol solution.

Five-[2-$^{14}$C]hydroxytryptamine (5-HT) (56.4 mCi/mmol) and [3-$^3$H]Sph (22.0 Ci/mmol) were obtained from DuPont—New England Nuclear, Boston, Mass.; Sph, ceramide (type III), acetylsalicylic acid, cytochalasin B, cytochalasin D, fibrinogen, thrombin and ADP were obtained from Sigma, St. Louis, Mo.; collagen and epinephrine were obtained from Chrono-Log, Havertown, Pa; and staurosporine and prostaglandin E$_1$ were obtained from Biomol, Plymouth Meeting, Pa.

Washed platelets were prepared as described previously (Yatomi et al. Biochim. Biophys. Acta 1212: 337, 1994). The platelets were resuspended in a buffer containing 138 mM NaCl, 3.3 mM NaH$_2$PO$_4$, 2.9 mM KCl, 1.0 mM MgCl$_2$, 1 mg/ml of glucose and 20 mM HEPES (pH 7.4). The suspensions were adjusted to $3 \times 10^8$/ml and supplemented with 1 mM CaCl$_2$ unless stated otherwise. For shape change studies, the platelets, after final centrifugation, were left for at least 60 min at 37° C. because that resulted in greater response. All experiments using intact platelet suspensions were performed at 37° C.

Those processes were monitored in a Platelet Ionized Calcium Aggregometer (Chrono-Log, Hayertown, Pa.) with stirring at 1000 rpm. The instrument was calibrated with a platelet suspension for zero light transmission and the buffer for 100% transmission. When aggregation was measured, human fibrinogen (500 μg/ml) was added to platelet suspensions shortly before the addition of stimuli, unless stated otherwise. The increase in light transmission caused by platelet aggregation (Zucker, Meth. Enzymol. 169: 117, 1989) was recorded continuously.

Shape change was observed by adding 5 mM EDTA (instead of Ca$^{2+}$) before administration of stimuli to prevent aggregation, and indicated by a decrease in light transmission (Zucker, Meth. Enzymol. 169: 117, 1989; Patscheke & Worner, Throm. Res. 12: 485, 1978).

For quantitative evaluation of both processes, results were expressed as the maximum change of light transmission within 5 min after stimulation.

Platelet suspensions (0.5 ml) were incubated with 1 μM [$^3$H]Sph (0.2 μCi). At the selected time points, the reaction was terminated by addition of 1.875 ml of ice-cold chloroform/methanol/concentrated HCl (100:200:1). The lipids were extracted from the cell suspensions and the phases separated by the method of Bligh and Dyer (Bligh & Dyer, Can. J. Biochem. Physiol. 37: 911, 1959). The upper aqueous phase samples were neutralized with NH$_4$OH and then dried completely. The lipids were recovered in 1 ml chloroform/methanol (2:1) with sonication.

After centrifugation at 1000×g for 10 min, the added chloroform/methanol was transferred to another tube and thus separated from precipitated salt. The desalinization procedure was repeated once. Finally, samples were dried and resuspended in small volumes of chloroform/methanol (2:1). The lower chloroform phase samples were dried and then resuspended in small volumes of chloroform/methanol (2:1).

Portions of lipids obtained from each phase were applied to silica gel 60 HPTLC plates (Merck, Darmstadt, Germany) and the plates were developed in chloroform/methanol/water (65:35:8) for upper phase separation and butanol/acetic acid/water (3:1:1) for lower phase separation, with appropriate standards. The bands were identified by staining the control lipids with primulin and visualizing under UV light.

After enhancer (Resolution TLC; E.M. Corp., Chestnut Hill, Mass) treatment of thin layer chromatography (TLC) plates, autoradiography was performed with Kodak X-Omat film at $-80°$ C. for 1–3 days. The silica gel areas containing the radiolabeled sphingolipids were scraped off and counted by liquid scintillation counting.

Under those conditions, ceramide was recovered completely in the lower phase; no ceramide bands were detected in upper phase samples. Recoveries in the lower phase of Sph and Sph-1-P were 85% and 50%, respectively. Furthermore, levels of Sph-1-P in the two phases always correlated well with each other.

When indicated, samples, at the appointed times, were centrifuged for 15 s at 12000×g. Lipids then were extracted from the resultant supernatant and cell pellet and analyzed as described above.

The cellular amounts of Sph-1-P were measured by quantitative conversion of Sph-1-P to $[^3H]C_2$-Cer-1-P (N-$[^3H]$ acetylated Sph-1-P) by acylation with $[^3H]$acetic anhydride.

Platelet suspensions were adjusted to $1-2 \times 10^9$/ml and to the 0.5 ml aliquots were added 3 ml of chloroform/methanol (1:2), followed by through mixing and sonication for 5 min. Phases were separated by further adding 2 ml of chloroform, 2 ml of 1M KCl and 100 µl $NH_4OH$. Three ml of chloroform and 200 µl of concentrated HCl were added to the alkaline upper phases, where over 50% of Sph-1-P shifted to the lower chloroform phases, which were evaporated under $N_2$.

The dried samples were dissolved in 40 µl of 0.008N NaOH in methanol/10 mM solution $[^3H]$acetic anhydride (1:1) by sonication. Acylation reactions were allowed to proceed at 37° C. for 1 or 2 h. The remaining anhydride was hydrolyzed by addition of 0.2 ml of 0.2N NaOH in methanol. Following a 1 h incubation at room temperature, the $C_2$-Cer-1-P formed was extracted by addition of 0.78 ml methanol, 0.98 ml chloroform, 0.9 ml 1M NaCl and 20 µl concentrated HCl. The lower chloroform phase was washed twice by 1 ml of chloroform/methanol/water (3/48/47) plus 10 µl of concentrated HCl.

Samples from the chloroform phase were evaporated under $N_2$ and then resuspended in small volumes chloroform/methanol (2:1). Portions of the lipids obtained were applied to silica gel 60 HPTLC plates and the plates were developed in butanol/acetic acid/water (3:1:1), chloroform/methanol/7N $NH_4OH$/water (80:20:0.5:0.5) or chloroform/methanol/acetic acid/water (65:43:1:3), with appropriate standards. The bands were identified by staining the control lipids with primulin and visualized under UV light. After enhancer (Resolution TLC) treatment of plates, autoradiography was performed with Kodak X-Omat film.

Radioactive spots corresponding to $[^3H]C_2$-Cer-1-P were scraped off and counted by liquid scintillation counting. Sph-1-P levels in cell extracts were calculated by extrapolation from Sph-1-P standards which were run through the same procedures.

Production of $C_2$-Cer-1-P was identified separately by fast atom bombardment mass spectrometry (FAB-MS) analysis using non-radioactive acetic anhydride. Furthermore, the product of N-acylation with $[^3H]$acetic anhydride of Sph-1-P, both prepared from sphingosylphosphocholine with phospholipase D and one extracted from platelets, coincided with the FAB-MS-identified $C_2$-Cer-1-P in the TLC mobility under three different solvent systems described above.

The lower chloroform samples, obtained when the phases were separated in the alkaline conditions for quantifying Sph-1-P mass (see above), were assayed for the mass measurement of Sph present in platelet extracts.

Platelets were suspended in 0.8 ml of the above-indicated buffer without $NaH_2PO_4$. Then, lipids were extracted as described previously (Cassella et al. Nature 293: 302, 1981) and assayed for phosphorous quantification, which was performed by the method of Chen et al. (Roth & Siok, J. Biol. Chem. 253: 3782, 1978).

Sph-1-P extracted from platelets was quantified by its conversion to $[^3H]C_2$-Cer-1-P by N-acylation with $[^3H]$ acetic anhydride. The mass of Sph-1-P in platelets was calculated as $1.42 \pm 0.05$ nmol/$10^9$ cells (mean±SD, n=3). On the other hand, the mass of Sph in platelets was $378 \pm 52$ pmol/$10^9$ cells (mean±SD, n=3). Accordingly, the amount of Sph-1-P present in platelets is about 4 times higher than that of Sph, the substrate of Sph kinase. The finding that the cellular content of Sph-1-P is much higher than that of Sph is consistent with the $[^3H]$Sph labeling studies. Furthermore, the mol % Sph-1-P/phospholipid value was calculated as $0.211 \pm 0.014$ (mean±SD, n=3) for platelets and over 10 times higher than the value for neutrophils, which was $0.0177 \pm 0.0028$ (mean±SD, n=3).

All references cited herein are incorporated expressly herein in entirety.

It will be evident to the artisan that various changes and modifications can be made to the instant invention without departing from the spirit thereof.

What is claimed is:

1. An assay for detecting a sphingosine comprising the steps of:
   (a) extracting lipids from a biologic sample;
   (b) treating said extracted lipids with alkali;
   (c) reacting said treated extracted lipids with labeled acyl anhydride to yield labeled N-acylated lipid derivatives;
   (d) separating said labeled N-acylated lipid derivatives in a pattern which discriminates said derivatives by label detection; and
   (e) comparing said pattern of discriminated labelled derivatives with a known pattern of labeled sphingosine separated as in step (d).

2. The assay of claim 1, wherein said alkali is sodium hydroxide.

3. The assay of claim 1, wherein said acyl anhydride is acetic anhydride or propionic anhydride.

4. The assay of claim 1, wherein said separating step (d) is by thin layer chromatography.

5. The assay of claim 1, wherein said sphingosine is sphingosine-1-phosphate.

6. The assay of claim 1, further comprising the step of treating the reaction mixture of step (c) with alkali.

7. The assay of claim 1, wherein the amount of labelled derivative of step (d) is measured.

8. The assay of claim 1, wherein said acyl anhydride is radiolabeled.

9. The assay of claim 8, wherein said radiolabeled acyl anhydride comprises $^{3}H$ or $^{14}C$.

10. An assay for determining platelet activation by quantifying sphingosine-1-phosphate in a first biologic sample comprising the steps of:

(a) extracting lipids from said first biologic sample following removal of platelets from said sample;

(b) treating said extracted lipids with alkali;

(c) reacting said treated, extracted lipids with labeled acyl anhydride to yield labeled N-acylated lipid derivatives;

(d) separating said labeled N-acylated lipid derivatives in a first pattern which discriminates said derivatives by label detection;

(e) comparing said first pattern of discriminated labeled derivatives with a second, control pattern of labeled sphingosine-1-phosphate separated as in step (d) and with a third, control pattern of labeled N-acylated lipid derivatives of a second biological sample containing non-activated platelets extracted, treated, reacted and separated as in steps (a), (b), (c) and (d) to identify labeled sphingosine-1-phosphate in said samples (f) measuring the amount of labeled sphingosine-1-phosphate in said first, second and third patterns, and (g) determining if platelets are activated in said first sample by the presence of sphingosine-1-phosphate in said first sample in an amount greater than found in said second sample.

11. The assay of claim 10, wherein said alkali is sodium hydroxide.

12. The assay of claim 10, wherein said acyl anhydride is acetic anhydride or propionic anhydride.

13. The assay of claim 10, wherein said separating step (d) is by thin layer chromatography.

14. The assay of claim 10, further comprising the step of treating the reaction mixture of step (c) with alkali.

15. The assay of claim 10, wherein said labeled acyl anhydride is radiolabeled.

16. The assay of claim 15, wherein said radiolabeled acyl anhydride comprises $^{3}H$ or $^{14}C$.

* * * * *

UNITED STATES PATENT AND TRADEMARK OFFICE
CERTIFICATE OF CORRECTION

PATENT NO. : 5,677,189
DATED : October 14, 1997
INVENTOR(S) : Yasuyuki Igarashi; Yutaka Yatomi; Hideki Ohta It is certified that error appears in the above-identified patent and that said Letters Patent is hereby corrected as shown below:

Column 9, line 36 delete "through", insert --thorough--.

Signed and Sealed this

Twenty-third Day of June, 1998

Attest:

BRUCE LEHMAN

*Attesting Officer*      *Commissioner of Patents and Trademarks*